(12) United States Patent
Dent, III et al.

(10) Patent No.: US 9,212,150 B2
(45) Date of Patent: Dec. 15, 2015

(54) PROCESS FOR THE PREPARATION OF CERTAIN TRIARYL PESTICIDE INTERMEDIATES

(71) Applicant: Dow AgroSciences LLC, Indianapolis, IN (US)

(72) Inventors: William Hunter Dent, III, Indianapolis, IN (US); Ronald Ross, Jr., Zionsville, IN (US); Anne M. Wilson, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 106 days.

(21) Appl. No.: 14/192,411

(22) Filed: Feb. 27, 2014

(65) Prior Publication Data
US 2014/0275557 A1 Sep. 18, 2014

Related U.S. Application Data

(60) Provisional application No. 61/778,543, filed on Mar. 13, 2013.

(51) Int. Cl.
*C07D 249/08* (2006.01)

(52) U.S. Cl.
CPC .................................. *C07D 249/08* (2013.01)

(58) Field of Classification Search
None
See application file for complete search history.

(56) References Cited

U.S. PATENT DOCUMENTS

| | | | |
|---|---|---|---|
| 5,187,185 A | 2/1993 | Outcalt et al. | |
| 5,304,657 A | 4/1994 | Toki et al. | |
| 5,530,021 A | 6/1996 | Yanagi et al. | |
| 5,726,324 A | 3/1998 | Huang et al. | |
| 6,166,243 A | 12/2000 | Jin et al. | |
| 6,258,973 B1 | 7/2001 | D'Silva et al. | |
| 6,392,081 B1 | 5/2002 | Ancel | |
| 6,410,737 B1 | 6/2002 | Ancel et al. | |
| 6,417,187 B2 | 7/2002 | Hegde et al. | |
| 7,094,906 B2 | 8/2006 | Ancel | |
| 7,323,574 B2 | 1/2008 | Ancel et al. | |
| 2005/0009834 A1 | 1/2005 | Itoh et al. | |
| 2007/0259962 A1 | 11/2007 | Deyn et al. | |
| 2008/0199606 A1 | 8/2008 | Karl et al. | |
| 2009/0209476 A1 * | 8/2009 | Crouse et al. | .................... 514/25 |
| 2012/0053216 A1 | 3/2012 | Creemer et al. | |
| 2012/0172217 A1 | 7/2012 | Brown et al. | |
| 2012/0172218 A1 | 7/2012 | Crouse et al. | |
| 2013/0019348 A1 | 1/2013 | Crouse et al. | |
| 2013/0030190 A1 | 1/2013 | Gharda | |

OTHER PUBLICATIONS

PCT International Search Report/Written Opinion for PCT/US2014/018995, completed May 20, 2014.

* cited by examiner

*Primary Examiner* — Alicia L Otton
(74) *Attorney, Agent, or Firm* — Carl D. Corvin; Barnes & Thornburg LLP

(57) ABSTRACT

Certain intermediates useful in the preparation of triaryl pesticides are prepared from a substituted phenyl hydrazine and a substituted benzaldehyde by a cyclization process.

6 Claims, No Drawings

PROCESS FOR THE PREPARATION OF CERTAIN TRIARYL PESTICIDE INTERMEDIATES

CROSS REFERENCE TO RELATED APPLICATIONS

This application claims the benefit of U.S. Provisional Patent Application Ser. No. 61/778,543 filed Mar. 13, 2013, the entire disclosure of which is hereby expressly incorporated by reference.

BACKGROUND OF THE INVENTION

The present invention concerns an improved process for preparing certain intermediates useful in the preparation of triaryl pesticides.

U.S. Pat. No. 8,178,658 (B2) describes, inter alia, certain triaryl rhamnose carbamates and their use as insecticides. Among the methods used to prepare such triaryl rhamnose carbamates are those which involve intermediates of the Formula I

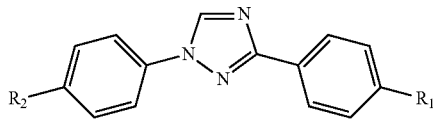

wherein $R_1$ represents $NO_2$ or $CO_2R_3$, $R_2$ represents $C_1$-$C_6$ haloalkoxy, and $R_3$ represents $C_1$-$C_6$ alkyl.

When $R_1$ is $NO_2$, the nitro group can be reduced to the amine, reacted with a chloroformate with a good leaving group, e.g., 4-nitrophenyl, and subsequently reacted with a rhamnose. When $R_1$ is $CO_2R_3$, the ester can be hydrolyzed to the acid, the acid can be converted to the benzoyl azide, the benzoyl azide can be converted to the isocyanate and the isocyanate can be treated with a rhamnose and a strong base. It would be desirable to have a process in which intermediates of Formula I could be prepared in good yield by a cyclization process.

SUMMARY OF THE INVENTION

The present invention provides such conditions. Thus, the present invention concerns a process for preparing triaryl pesticide intermediates of the Formula (I),

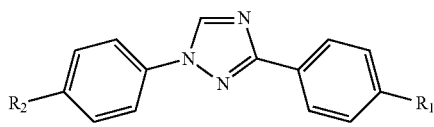

wherein $R_1$ represents $NO_2$ or $CO_2R_3$, $R_2$ represents $C_1$-$C_6$ haloalkoxy, and $R_3$ represents $C_1$-$C_6$ alkyl which comprises:

a) contacting a substituted phenyl hydrazine of Formula (II)

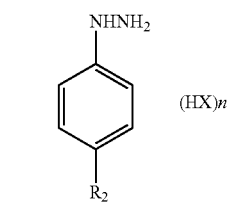

wherein $R_2$ is as previously defined,

X represents Cl or Br, and n=0, 1 or 2, with a substituted benzaldehyde of Formula (III)

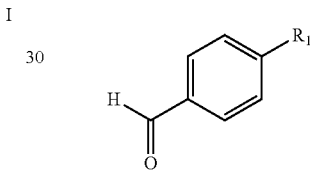

wherein $R_1$ is as previously defined, in an inert organic solvent to provide a hydrazone of Formula (IV)

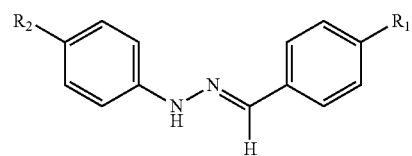

wherein $R_1$ and $R_2$ are as previously defined;

b) chlorinating or brominating the hydrazone of Formula (IV) with a chlorinating or brominating agent in the presence of a sulfide in an inert organic solvent to provide a halohydrazone of Formula (V)

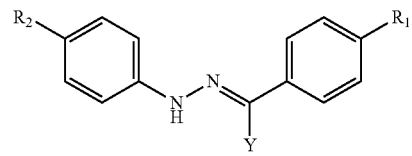

wherein

R$_1$ and R$_2$ are as previously defined, and

Y represents Cl or Br; and c) contacting the halohydrazone of Formula (V) with an amine of formula

wherein

R$_4$ represents H, Si(CH$_3$)$_3$ or CH(C$_6$H$_5$)$_2$ in the presence of an organic base followed by oxidizing with an oxidizing agent.

DETAILED DESCRIPTION OF THE INVENTION

Throughout this document, all temperatures are given in degrees Celsius, and all percentages are weight percentages unless otherwise stated.

The term "alkyl", as well as derivative terms such as "haloalkoxy", as used herein, include within their scope straight chain, branched chain and cyclic moieties. Thus, typical alkyl groups are methyl, ethyl, propyl, butyl, pentyl, hexyl, 1-methylethyl, 1,1-dimethylethyl, 1-methylpropyl, 2-methylpropyl, cyclopropyl, cyclobutyl, cyclopentyl and cyclohexyl. The term "haloalkoxy" includes alkoxy groups substituted with from one to the maximum possible number of halogen atoms, all combinations of halogens included. Unless specifically defined otherwise, the term "halogen" or "halo" includes fluorine, chlorine, bromine and iodine, with fluorine being preferred.

The present invention concerns a process for preparing certain triaryl pesticide intermediates of the Formula (I),

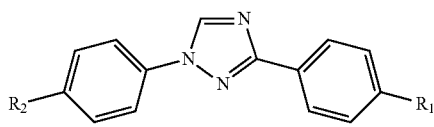

wherein

R$_1$ represents NO$_2$ or CO$_2$R$_3$,

R$_2$ represents C$_1$-C$_6$ haloalkoxy, and

R$_3$ represents C$_1$-C$_6$ alkyl from a substituted phenyl hydrazine of Formula (II)

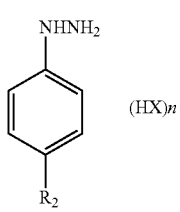

wherein

R$_2$ is as previously defined,

X represents Cl or Br, and n=0, 1 or 2, and a substituted benzaldehyde of Formula (III)

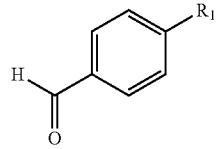

wherein

R$_1$ is as previously defined, by formation of a hydrazone of Formula (IV)

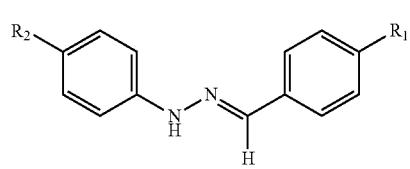

wherein

R$_1$ and R$_2$ are as previously defined, followed by chlorination or bromination to provide a halohydrazone of Formula (V)

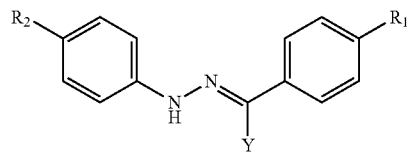

wherein

R$_1$ and R$_2$ are as previously defined, and

Y represents Cl or Br, and by addition of an amine of formula

wherein

R$_4$ represents H, Si(CH$_3$)$_3$ or CH(C$_6$H$_5$)$_2$ followed by oxidation.

R$_2$ is preferably OCF$_3$ or OCF$_2$CF$_3$.

R$_3$ is preferably CH$_3$.

R$_4$ is preferably Si(CH$_3$)$_3$.

In the hydrazone formation, a substituted phenyl hydrazine of Formula (II)

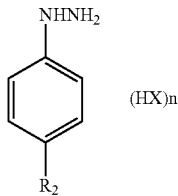

II wherein
$R_2$ is as previously defined,
X represents Cl or Br, and
n=0, 1 or 2,
is reacted with a substituted benzaldehyde of Formula (III)

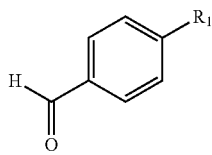

III wherein
$R_1$ is as previously defined.

The hydrazone formation can be conducted in water or any inert organic solvent including alcohols such as ethanol (EtOH), chlorinated hydrocarbons such as dichloromethane (CH$_2$Cl$_2$), aromatic hydrocarbons such as toluene, organic acids such as acetic acid and polar aprotic solvents such as dimethyl sulfoxide (DMSO). Preferred solvents are polar solvents, especially alcohols like methanol (MeOH), EtOH, and propanol.

The hydrazone formation requires stoichiometric amounts of substituted phenyl hydrazine and substituted benzaldehyde, although a slight excess of either reagent can be used.

The hydrazone formation is conducted at a temperature from about 0° C. to about 70° C., with room temperature being preferred.

In a typical reaction, the substituted benzaldehyde is dissolved in the solvent and the substituted phenyl hydrazine is added. The reaction is stirred at room temperature until the reaction is completed. The solvent is evaporated under reduced pressure and the residue is dried under vacuum to give the desired hydrazone.

In the chlorination or bromination reaction, the hydrazone is chlorinated or brominated with a chlorinating or brominating agent in the presence of a sulfide in an inert organic solvent to provide a halohydrazone of Formula (V)

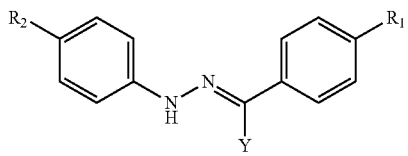

V wherein
$R_1$ and $R_2$ are as previously defined, and
Y represents Cl or Br.

Typical chlorinating or brominating agents can be used in the chlorination or bromination reaction, including chlorine, bromine, N-chlorosuccinamide, N-bromosuccinamide, 1,3-dichloro-5,5-dimethyl hydantoin, CuCl$_2$ or Ph$_3$P/CCl$_4$. N-Chlorosuccinamide and 1,3-dichloro-5,5-dimethyl hydantoin are particularly preferred.

The chlorination or bromination is conducted in an inert organic solvent with a freezing point well below 0° C., for example, alcohols such as EtOH, ethers such as tetrahydrofuran (THF), esters, such as ethyl acetate (EtOAc) and nitriles such as acetonitrile (MeCN). Chlorinated hydrocarbon solvents such as CH$_2$Cl$_2$, chloroform and dichloroethane are especially preferred.

While the chlorination or bromination requires only one equivalent of chlorinating or brominating agent, excesses of about 50 mol % are often employed. The chlorination/bromination is conducted in the presence of a sulfide, preferably a dialkyl sulfide of from about 2 to about 8 total carbon atoms such as dimethyl sulfide, diethyl sulfide or thiane (pentamethylene sulfide). Typically, from about 1 to about 5 equivalents of sulfide is used for each equivalent of chlorinating or brominating agent.

The chlorination or bromination is conducted at a temperature from about −90° C. to about 0° C., with a temperature from about −80° C. to about −35° C. being preferred.

In a typical reaction, N-chlorosuccinamide and dimethyl sulfide are added to CH$_2$Cl$_2$ at about 0° C. The mixture is then cooled to about −78° C. and the hydrazone in CH$_2$Cl$_2$ is slowly added. The mixture is stirred until the reaction is completed and allowed to warm to room temperature. The solvent is evaporated and the isolated product purified by conventional techniques such as flash chromatography.

In the addition/cyclization sequence of reactions, the chlorohydrazone is initially treated with an amine (amine addition reaction) of formula $R_4CH_2NH_2$ wherein
$R_4$ represents H, Si(CH$_3$)$_3$ or CH(C$_6$H$_5$)$_2$.

The amine addition is run in a polar aprotic solvent, which includes amides, like N,N-dimethylformamide (DMF), N,N-dimethylacetamide (DMA) or N-methyl-2-pyrrolidinone (NMP), ethers like THF, dioxane and dimethoxyethane, sulfoxides, like DMSO, esters, like EtOAc, and nitriles, like MeCN, propionitrile or butyronitrile. MeCN is particularly preferred.

While the amine addition requires only one equivalent of amine, slight excesses of up to about 10 mol % are often employed. The amine addition is conducted in the presence of an organic base. Preferred organic bases are non-nucleophilic. Tertiary amine bases such as triethylamine (TEA) are most preferred. While the amine addition requires only about 1 equivalent of organic base, slight excesses of up to about 10 mol % are often employed.

The amine addition is conducted at a temperature from ambient to about 50° C., with room temperature being preferred.

In a typical reaction, the halohydrazone is dissolved in MeCN and the amine and organic base are added. The mixture is stirred at room temperature until the starting materials are consumed. The solvent is evaporated and the isolated product used, as is, in the subsequent oxidation reaction.

In the oxidation stage of the addition/cyclization sequence of reactions, the product of the amine addition reaction is contacted with an oxidizing agent to provide the desired triaryl pesticide intermediates. Typical oxidizing agents include sodium hypochlorite (NaOCl), calcium hypochlorite (Ca(OCl)$_2$), silver carbonate (Ag$_2$CO$_3$), Dess-Martin periodinane (DMPI) and tetrapropylammonium perruthenate/N-methylmorpholine N-oxide (TPAP/NMO). NaOCl, Ca(OCl)$_2$ and Ag$_2$(CO$_3$) are often preferred oxidizing agents. While the oxidation requires only one equivalent of oxidizing agent, excesses of about 1.5 to about 3 equivalents are often employed.

The oxidation stage is conveniently conducted in the same solvent as the amine addition reaction. Similarly, MeCN is particularly preferred.

The oxidation is conducted at a temperature from ambient to about 50° C., with room temperature being preferred.

In a typical reaction sequence, the initial product of the amine addition reaction is dissolved in MeCN and the oxidizing agent is added. The mixture is stirred at room temperature until the reaction is complete. The reaction mixture is diluted with a water immiscible solvent and washed with water. The solvent is evaporated and the isolated triaryl pesticide intermediates are purified by conventional techniques such as flash chromatography.

The following examples are presented to illustrate the invention.

EXAMPLES

Example 1

Preparation of (E)-Methyl 4-((2-(4-(trifluoromethoxy)phenyl) hydrazono)methyl)benzoate

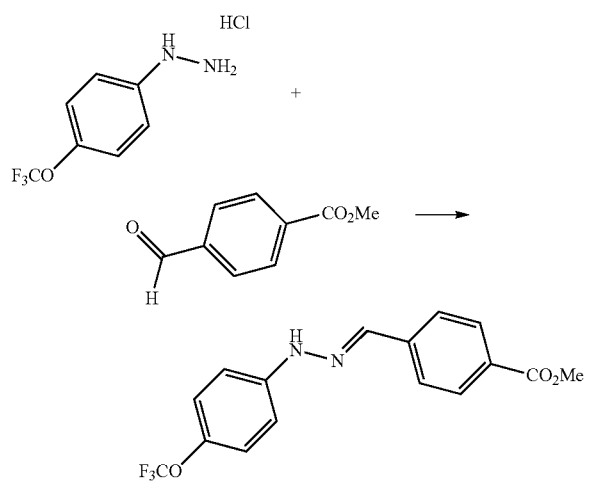

To a magnetically stirred solution of methyl 4-formylbenzoate (1.71 g, 10.41 mmoL) dissolved in EtOH (mL) was added (4-(trifluoromethoxy)phenyl)-hydrazine hydrochloride (2 g, 10.41 mmoL) and the reaction was stirred at room temperature overnight. The solvent was concentrated under reduced pressure and dried under high vacuum to give (E)-methyl 4-((2-(4-(trifluoromethoxy)phenyl)-hydrazono)methyl)benzoate (3.08 g, 87%): mp 142-145° C.; $^1$H NMR (400 MHz, CDCl$_3$) δ 10.10 (s, 1H), 8.04 (d, J=8.0 Hz, 2H), 7.72-7.65 (m, 3H), 7.13 (q, J=8.9 Hz, 4H), 3.93 (s, 3H); $^{19}$F NMR (376 MHz, CDCl$_3$) δ −58.36; ESIMS m/z 338 ([M+H])$^+$.

Example 2

Preparation of (E and Z)-Methyl 4-(chloro(2-(4-(trifluoromethoxy)phenyl)hydrazono)methyl)benzoate

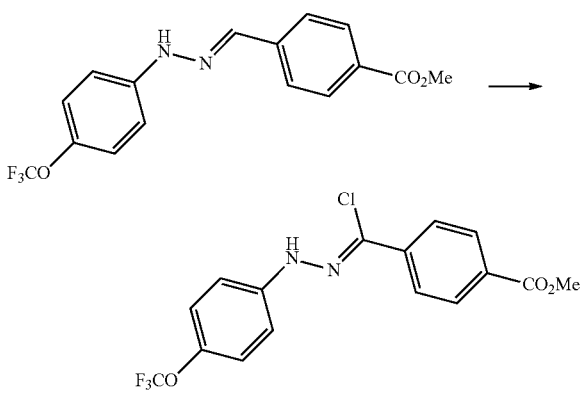

To a magnetically stirred solution of N-chlorosuccinimide (0.59 g, 4.43 mmoL) in CH$_2$Cl$_2$ (8 mL) at 0° C. was added dimethyl sulfide (0.85 mL, 8.87 mmoL) and the reaction mixture was stirred for 15 minutes (min) and then cooled to −78° C. To this solution was added (E)-methyl 4-((2-(4-(trifluoromethoxy)-phenyl)hydrazono) methyl)benzoate dissolved in 8 mL of CH$_2$Cl$_2$ and the reaction mixture was stirred at this temperature for 1 hour (h), warmed to room temperature and stirred for 2 h. The solution was concentrated under reduced pressure. The residue was dissolved in CH$_2$Cl$_2$ (15 mL) and added to a silica gel (SiO$_2$) loading cartridge and purified via flash column chromatography (Gradient EtOAc/hexanes). The title compound was obtained as a yellow solid as a mixture of E and Z isomers: mp 159-162° C.; $^1$H NMR (400 MHz, CDCl$_3$) δ 8.18 (s, 1H), 8.07 (d, J=8.8 Hz, 2H), 7.98 (d, J=8.8 Hz, 2H), 7.20 (s, 4H), 3.95 (s, 3H); $^{19}$F NMR (376 MHz, CDCl$_3$) δ−58.32; ESIMS m/z 372 ([M+H])$^+$.

Example 3

Preparation of Methyl 4-(1-(4-(trifluoromethoxy)phenyl)-1H-1,2,4-triazol-3-yl)benzoate

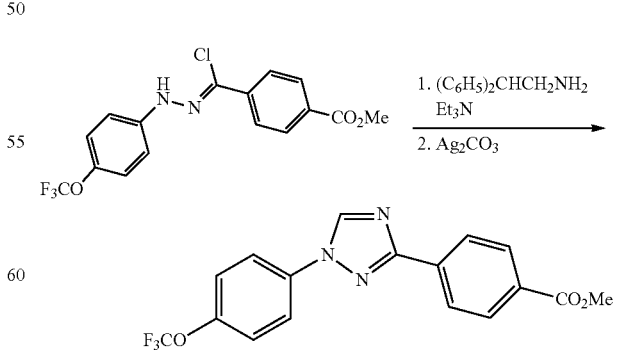

To a magnetically stirred solution of methyl 4-(chloro(2-(4-(trifluoromethoxy)phenyl)hydrazono)methyl)benzoate (150 mg, 0.402 mmoL) in MeCN (2 mL) was added 2,2- diphenylethyl amine (87 mg; 0.443 mmoL) followed by TEA (62 µL, 0.443 mmoL) and the reaction mixture was stirred overnight to give the crude triazene. The solvent was concentrated under reduced pressure. The residue was dissolved in fresh MeCN (2 mL) and Ag$_2$CO$_3$ (166 mg, 0.604 mmoL) was added and the reaction was stirred at room temperature for 5 h. The solvent was evaporated and the residue taken up in 2:1 EtOAc/hexane. The mixture was filtered followed by purification via radial chromatography using a 2:1 EtOAc/hexane mixture as the eluent. The title compound was isolated from the fraction at R$_f$=0.35 (63 mg, 43%): mp 165-168° C.; $^1$H NMR (400 MHz, CDCl$_3$) δ 8.60 (s, 1H), 8.28 (d, J=8.7 Hz, 2H), 8.15 (d, J=8.7 Hz, 2H), 7.82 (d, J=9.1 Hz, 2H), 7.40 (d, J=9.0 Hz, 2H), 3.96 (s, 3H); $^{19}$F NMR (376 MHz, CDCl$_3$) δ −58.01; $^{13}$C NMR (101 MHz, CDCl$_3$) δ 166.76, 162.61, 148.55, 141.77, 135.41, 134.46, 131.03, 130.02, 126.46 122.44, 121.66, 121.31, 119.10; GCMS m/z 363 [M$^+$].

Example 4

Preparation of Methyl 4-(1-(4-(trifluoromethoxy)phenyl)-1H-1,2,4-triazol-3-yl)benzoate

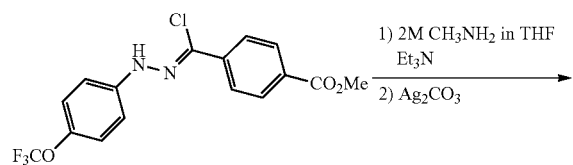

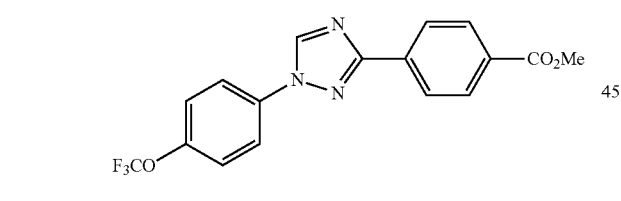

1.5 equiv. of Ag$_2$CO$_3$ (25%)
3 equiv. of Ag$_2$CO$_3$ (55%)

To a magnetically stirred solution of methyl 4-(chloro(2-(4-(trifluoromethoxy)phenyl)hydrazono)methyl)benzoate (123 mg; 0.330 mmoL) in MeCN (1.6 mL) was added methyl amine (2.0 M in THF; 0.2 mL, 0.363 mmoL) followed by TEA (51 µL, 0.363 mmoL) and the reaction mixture was stirred overnight to give the crude triazene. The solvent was concentrated under reduced pressure. The residue was dissolved in fresh MeCN (1.6 mL) and Ag$_2$CO$_3$ (1.5 eq.; 136 mg, 0.495 mmoL) (3 eq.; 272 mg; 0.99 mmoL) was added in two separate reactions and each was stirred at room temperature for 5 h. The solvent was evaporated from each and the residues taken up in 2:1 EtOAc/hexane. The mixtures were filtered followed by purification via radial chromatography using a 2:1 EtOAc/hexane mixture as the eluent. The title compound was isolated from the fraction at R$_f$=0.35 (1.5 eq. of Ag$_2$CO$_3$; 30 mg, 25%) (3 eq. of Ag$_2$CO$_3$; 66 mg, 55%); mp 165-168° C.

Example 5

Preparation of Methyl 4-(1-(4-(trifluoromethoxy)phenyl)-1H-1,2,4-triazol-3-yl)benzoate

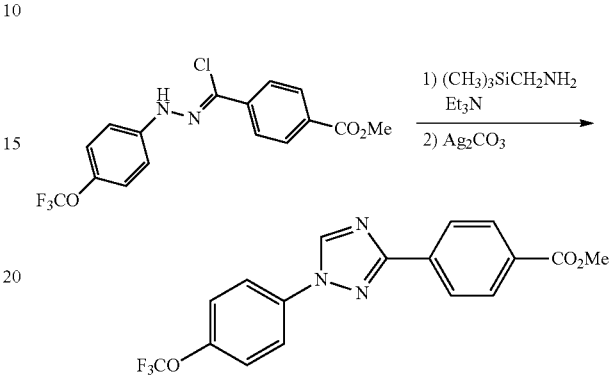

To a magnetically stirred solution of methyl 4-(chloro(2-(4-(trifluoromethoxy)phenyl)hydrazono)methyl)benzoate (125 mg, 0.335 mmoL) in MeCN (1.6 mL) was added trimethylsilylmethyl amine (38 mg, 0.369 mmoL) followed by TEA (52 µL, 0.369 mmoL) and the reaction mixture was stirred overnight to give the crude triazene. The solvent was concentrated under reduced pressure. The residue was dissolved in fresh MeCN (1.6 mL) and Ag$_2$CO$_3$ (139 mg; 0.503 mmoL) was added and the reaction was stirred at room temperature for 5 h. The solvent was evaporated and the residue taken up in 2:1 EtOAc/hexane. The mixture was filtered followed by purification via radial chromatography using a 2:1 EtOAc/hexane mixture as the eluent. The title compound was isolated from the fraction at R$_f$=0.35 (60 mg, 51%): mp 165-168° C.

Example 6

Preparation of Methyl 4-(1-(4-(trifluoromethoxy)phenyl)-1H-1,2,4-triazol-3-yl)benzoate

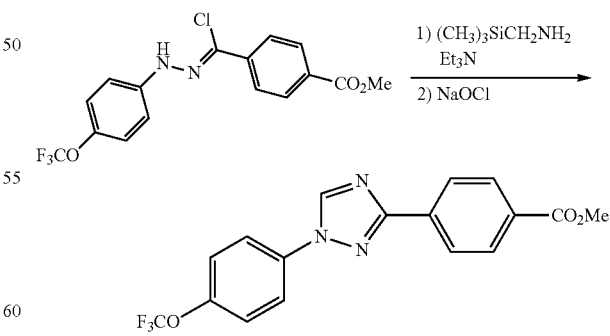

To a magnetically stirred solution of methyl 4-(chloro(2-(4-(trifluoromethoxy)phenyl)hydrazono)methyl)benzoate (125 mg, 0.335 mmoL) in MeCN (1.3 mL) was added trimethylsilylmethyl amine (38 mg, 0.369 mmoL) followed by TEA (52 µL, 0.369 mmoL) and the reaction mixture was stirred overnight to give the crude triazene. The solvent was concentrated under reduced pressure. The residue was dissolved in fresh MeCN (1.3 mL) and aqueous NaOCl solution (15%, 1.3 mL) and the reaction was stirred at room temperature for 24 hr. The mixture was diluted with EtOAc and washed with water. The organic layer was filtered, dried over magnesium sulfate (MgSO$_4$) and concentrated. The residue was purified via radial chromatography using a 3:1 hexane/EtOAc mixture to elute the impurities followed by increasing to 1:1 to elute the product. The title compound was isolated from the fraction at R$_f$=0.35 (58 mg, 60%): mp 165-168° C.

The same procedure outlined in Example 6 was used to obtain the triazole product using methyl amine (35% triazole yield), and 2,2-diphenylethyl amine (41% triazole yield) as the starting amine inputs in place of trimethylsilylmethyl amine.

Example 7

Preparation of 1-(4-Nitrobenzylidene)-2-(4-(trifluoromethoxy)phenyl)hydrazine

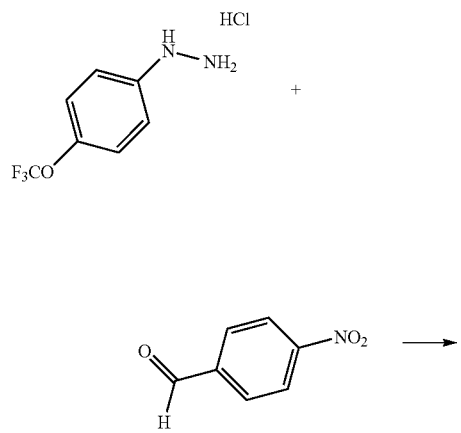

To a magnetically stirred solution of 4-nitrobenzaldehyde (1.57 g, 10.41 mmoL) dissolved in EtOH (21 mL) was added (4-(trifluoromethoxy)phenyl)-hydrazine (2 g, 10.41 mmoL) and the reaction was stirred at room temperature overnight. The solvent was concentrated under reduced pressure and dried under high vacuum to give the title compound as a mixture of E and Z-isomers (3.35 g, 99%): $^1$H NMR (400 MHz, CDCl$_3$) δ 10.17 (s, 1H), 8.40 (d, J=8.6 Hz, 2H, isomer A), 8.24 (d, J=8.6 Hz, 2H, isomer B), 8.08 (d, J=8.7 Hz, 2H, isomer A), 7.79-7.74 (m, 4H, mixture of isomers A & B), 7.19-7.13 (m, 6H, mixture of isomers A & B); $^{19}$F NMR (376 MHz, CDCl$_3$) δ −58.34; ESIMS m/z 325 ([M+H])$^+$.

Example 8

Preparation of 4-Nitro-N'-(4-(trifluoromethoxy)phenyl)-benzohydrazonoyl chloride

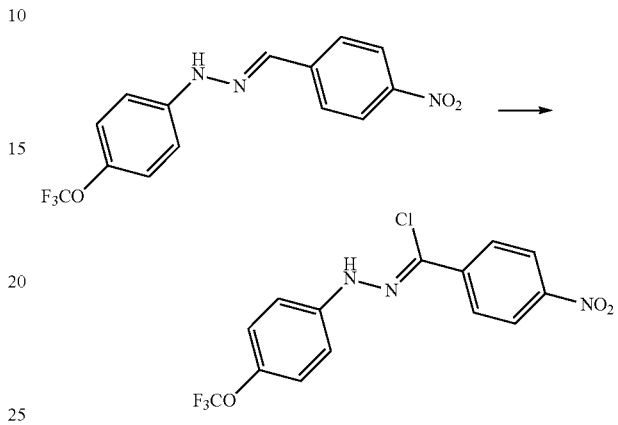

To a magnetically stirred solution of N-chlorosuccinimide (1.23 g, 9.22 mmoL) in CH$_2$Cl$_2$ (16 mL) at 0° C. was added dimethyl sulfide (1.36 mL, 18.45 mmoL) and the reaction mixture was stirred for 15 min and then cooled to −78° C. To this solution was added 1-(4-nitrobenzylidene)-2-(4-(trifluoromethoxy)-phenyl)hydrazine (2 g, 6.15 mmoL) dissolved in CH$_2$Cl$_2$ (16 mL) and the reaction mixture was stirred at this temperature for 1 h, warmed to room temperature and stirred for 2 h. The solution was concentrated under reduced pressure. The residue was dissolved in CH$_2$Cl$_2$ (15 mL) and added to a SiO$_2$ loading cartridge and purified via flash column chromatography (Gradient EtOAc/hexanes). The title compound was isolated as a yellow solid: mp 172-175° C.; $^1$H NMR (400 MHz, CDCl$_3$) δ 8.29-8.26 (m, 3H), 8.09-8.05 (m, 3H), 7.22 (s, 4H); $^{19}$F NMR (376 MHz, CDCl$_3$) δ −58.30; ESIMS m/z 359 ([M+H])$^+$.

Example 9

Preparation of 3-(4-Nitrophenyl)-1-(4-(trifluoromethoxy)-phenyl)-1H-1,2,4-triazole

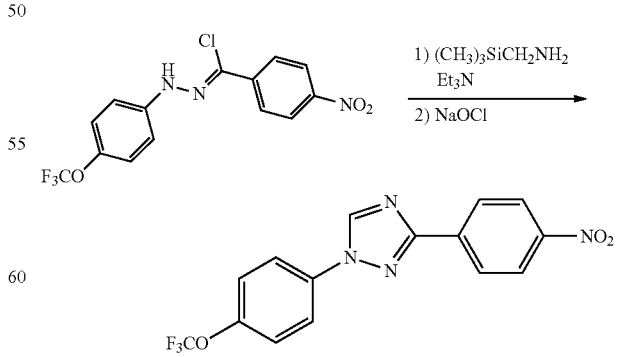

To a magnetically stirred solution of 4-nitro-N'-(4-(trifluoromethoxy)-phenyl)benzohydrazonoyl chloride (89 mg, 0.247 mmoL) in MeCN (1.2 mL) was added trimethylsilylmethyl amine (28 mg, 0.272 mmoL) followed by TEA (38 μL, 0.272 mmoL) and the reaction mixture was stirred overnight to give the crude triazene. The solvent was concentrated under reduced pressure. The residue was dissolved in fresh MeCN (1.2 mL) and NaOCl solution (15% Aldrich, 1.3 mL) and the reaction was stirred at room temperature for 24 h. The mixture was diluted with EtOAc and washed with water. The organic layer was filtered, dried over MgSO$_4$ and concentrated. The residue was dissolved in CH$_2$Cl$_2$ (5 mL) and added to a SiO$_2$ loading cartridge and purified via flash column chromatography (Gradient EtOAc/hexanes). The title compound was isolated as an orange solid: $^1$H NMR (400 MHz, CDCl$_3$) δ 8.63 (s, 1H), 8.45-8.27 (m, 4H), 7.93-7.73 (m, 2H), 7.42 (d, J=8.5 Hz, 2H); $^{13}$C NMR (101 MHz, CDCl$_3$) δ 172.76, 153.40, 148.53, 142.08, 136.30, 135.23, 127.31, 124.06, 123.95, 122.50, 121.40; ESIMS m/z 350 ([M+H])$^+$.

Example 10

Preparation of 3-(4-Nitrophenyl)-1-(4-(trifluoromethoxy)-phenyl)-1H-1,2,4-triazole

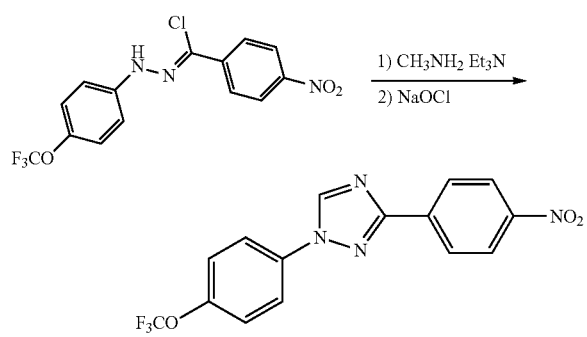

To a magnetically stirred solution of 4-nitro-N'-(4-(trifluoromethoxy)-phenyl)benzohydrazonoyl chloride (70 mg, 0.195 mmoL) in MeCN (1 mL) was added methyl amine (2M in THF; 0.1 mL, 0.207 mmoL) followed by TEA (81 μL, 0.584 mmoL) and the reaction mixture was stirred overnight to give the crude triazene. The solvent was concentrated under reduced pressure. The residue was dissolved in fresh MeCN (1 mL) and NaOCl solution (15% Aldrich, 1 mL) and the reaction was stirred at room temperature for 24 h. The mixture was diluted with EtOAc and washed with water. The organic layer was filtered, dried over MgSO$_4$ and concentrated. The residue was purified via radial chromatography using a 50% EtOAc/hexane as eluent. The title compound was isolated from the fraction at R$_f$=0.20 (13 mg, 28%).

Example 11

Preparation of 3-(4-Nitrophenyl)-1-(4-(trifluoromethoxy)-phenyl)-1H-1,2,4-triazole

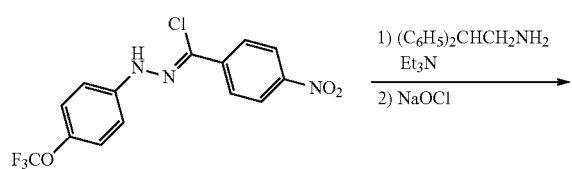

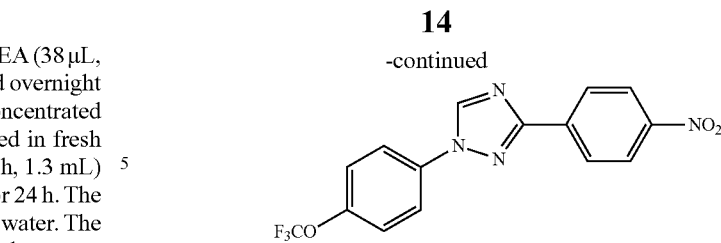

To a magnetically stirred solution of 4-nitro-N'-(4-(trifluoromethoxy)-phenyl)benzohydrazonoyl chloride (100 mg, 0.278 mmoL) in MeCN (1.4 mL) was added 2,2-diphenylethyl amine (60 mg, 0.306 mmoL) followed by TEA (43 μL, 0.306 mmoL) and the reaction mixture was stirred overnight to give the crude triazene. The solvent was concentrated under reduced pressure. The residue was dissolved in fresh MeCN (1.4 mL) and NaOCl solution (15% Aldrich, 1.3 mL) and the reaction was stirred at room temperature for 24 h. The mixture was diluted with EtOAc and washed with water. The organic layer was filtered, dried over MgSO$_4$ and concentrated. The residue was purified via radial chromatography using a 50% EtOAc/hexane as eluent. The title compound was isolated from the fraction at R$_f$=0.20 (48 mg, 50%).

What is claimed is:

1. A process for preparing triaryl pesticide intermediates of the Formula (I),

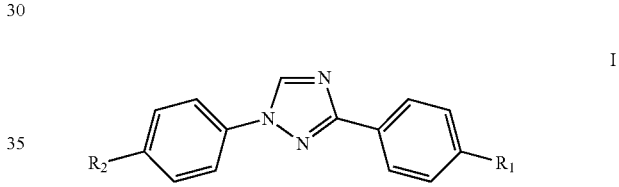

wherein
R$_1$ represents NO$_2$ or CO$_2$R$_3$,
R$_2$ represents C$_1$-C$_6$ haloalkoxy, and
R$_3$ represents C$_1$-C$_6$ alkyl
which comprises:
a) contacting a substituted phenyl hydrazine of Formula (II)

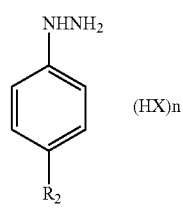

wherein
R$_2$ is as previously defined,
X represents Cl or Br, and
n=0, 1 or 2,
with a substituted benzaldehyde of Formula (III)

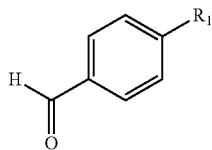

III wherein
R₁ is as previously defined,
in an inert organic solvent to provide a hydrazone of Formula (IV)

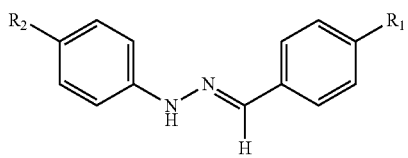

IV wherein
R₁ and R₂ are as previously defined;
b) chlorinating or brominating the hydrazone of Formula (IV) with a chlorinating or brominating agent in the presence of a sulfide in an inert organic solvent to provide a halohydrazone of Formula (V)

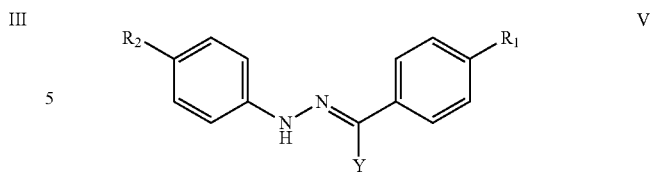

V wherein
R₁ and R₂ are as previously defined, and
Y represents Cl or Br; and
c) contacting the halohydrazone of Formula (V) with an amine of formula

R₄CH₂NH₂ wherein
R₄ represents H, Si(CH₃)₃ or CH(C₆H₅)₂
in the presence of an organic base followed by oxidizing with an oxidizing agent.

2. The process of claim 1 in which R₂ is OCF₃ or OCF₂CF₃.

3. The process of claim 1 in which R₃ is CH₃.

4. The process of claim 1 in which R₄ is Si(CH₃)₃.

5. The process of claim 1 in which the chlorinating or brominating agent is N-chlorosuccinamide or 1,3-dichloro-5,5-dimethyl hydantoin.

6. The process of claim 1 in which the oxidizing agent is NaOCl, Ca(OCl)₂ or Ag₂(CO₃).

\* \* \* \* \*